United States Patent
Ashkinazi

(10) Patent No.: US 6,340,755 B1
(45) Date of Patent: Jan. 22, 2002

(54) 5H-PYRANO[2,3-D: 6,5-D']DIPYRIMIDINE DERIVATIVES HAVING AN ANTIBACTERIAL, ANTIVIRAL AND IMMUNO-MODULATING ACTIVITY

(75) Inventor: Rimma Ilinichna Ashkinazi, Nevskii (RU)

(73) Assignee: Natural Drug Sciences LLC, Ramsey, NJ (US)

(*) Notice: Subject to any disclaimer, the term of this patent is extended or adjusted under 35 U.S.C. 154(b) by 0 days.

(21) Appl. No.: 09/554,836

(22) PCT Filed: Nov. 19, 1997

(86) PCT No.: PCT/RU97/00371

§ 371 Date: Jul. 31, 2000

§ 102(e) Date: Jul. 31, 2000

(87) PCT Pub. No.: WO99/25718

PCT Pub. Date: May 27, 1999

(51) Int. Cl.$^7$ .................. C07D 491/052; A61P 31/04; A61P 31/22

(52) U.S. Cl. ..................................... 544/251

(58) Field of Search ........................... 544/251

(56) References Cited

U.S. PATENT DOCUMENTS 4,272,534 A  6/1981  Blythin ................. 424/248.54

FOREIGN PATENT DOCUMENTS

DE   1952179   1/1996
EP   0541404   12/1993

OTHER PUBLICATIONS

Moskvin, A. V.; Sibgatullina, A. A.; Ivin, B. A., Russian J. Gen. Chem., 65(12) 1995, 1878–1882.*

Moskvin, A.V. et al., "Azoles and Azines: CVII. Synthesis of 5H–Pyrano[3–d:6,5–d]–dipyrimidine–2,4,6,8(1H,3H,7H, 9H)–tetraones and Their 2,8–Dithio Analogs," *Russian Journal of General Chemistry*:1300–1305 (1998).

* cited by examiner

*Primary Examiner*—Mukund J. Shah
*Assistant Examiner*—Thomas C McKenzie
(74) *Attorney, Agent, or Firm*—Gibbons, Del Deo, Doan, Griffinger & Vecchione

(57) ABSTRACT

The present invention relates to novel compounds having the formula

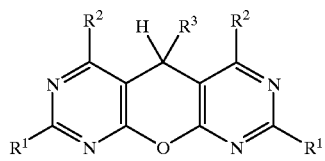

The compounds have antibacterial, antiviral, and immuno-modulating activity.

10 Claims, No Drawings

5H-PYRANO[2,3-D: 6,5-D']DIPYRIMIDINE DERIVATIVES HAVING AN ANTIBACTERIAL, ANTIVIRAL AND IMMUNO-MODULATING ACTIVITY

FIELD OF THE INVENTION

The invention relates to the area of organic chemistry and medicine, specifically to barbituric acids and their derivatives, and is designed for use as substances having antiviral, antichlamydic, immunomodulating and antitumoral activity.

DESCRIPTION OF PRIOR ART

Many derivatives of barbituric acid are biologically active substances. The derivatives of pyrimidine are nucleic bases (uracil, thymine, cytosine), vitamins (thiamine, phosphothiamine), coenzymes (cocarboxylase), and they are utilized as pharmaceuticals having soporific, anticonvulsive (barbiturates, hexamidine, benzonal), diuretic (mercusal), antiinflammatory (pentoxil, methyluracil), and antithyroidal (methylthiouracil) actions; they are synthetic analogs of vitamins ("bephothiamine"), anabolic (orotic acid), anti-inflammatory and antibacterial (sulfazin, sulfadimethazin, sulfamonomethoxin, sulfadimethoxin, bactrim, salazodimethoxin), antimalarial (chloridin), anticarcinogenic (dopan, phosphamide, ethimidide, fluorouracil, fluorofur, cytarabin) substances [1, 2].

In recent decades, systems in which the pyrimidine ring is condensed with other heterocycles have received considerable attention. Such heterocycles are frequently analogs of natural, biologically active substances. They include purines, which occur in natural and synthetic biologically active substances: nucleic acids (adenine, guanine), ATP, substances that excite the central nervous system (caffeine, theobromine, theophylline, "nihexine," diprophylline, xanthinol nictoninate), substances used in suppressing tissue incompatibility in organ transplants (azathioprine) (cytostatic and immunodepressive effect), and substances having an anabolic (inosine) or antileukemic effect (mercaptopurine), pyrazolo[3,4-d]pyrimidines used to treat diseases accompanied by hyperuremia (allopurinol); pteridines, used as diuretics (triamterene), vitamins (riboflavin, folic acid), anticarcinogenic drugs (methotrexate); pyrimido[5,4-d]pyrimidines having vasodilational properties (dipyridamole [1, 2].

Data on the biological activity of the most varied derivatives of 5-ylidenebarbituric acids have been summarized in a review [3] which notes the anticoma, antimicrobial, spasmolytic, antipyretic and antitumor activity of these substances. Data has also been obtained on the biological activity of certain 5-arylidenebarbituric acids [4–11], 5-aminomethylenebarbituric acids [12], products of the reaction of barbituric acids with isocyanates, isothiocynates - 5-arylcarbamoylbarbituric acids [13–16], pyrazolo[3,4-d]pyrimidines obtained by the condensation of 6-hydrainouracils with iso(thio)cyanates [17], 5-deazaflavins [18–20], condensation products of 6-aminouracils with nitrosobenzene-10-alkyl (halogenophenyl)-3-methylflavins [21, 22], derivatives of pyrrolo[2,3-d]pyrimidines [23], 7-methyl-5-hexyl-1H-pyrazolo-[3,4-d]-pyrimidino-4,6(5H,7H)-dion obtained by the action of Wilsmeyer's reagent on the corresponding 6-hydrazinouracil [24], pyrano[2,3-d]pyrimidines [25–27], 5-(3-nitrophenyl)-4-oxo-2-thioxo-1,3,7-triphenyl-1,2,3,4-tetrahydropyrido[2,3-d]pyrimidines [28–33],pyrimido[5,4-e][1,2,4]triazino-5,7(1H,6H)-dions [34], 5-dialkylaminomethylpyridines [35, 36], and pyrimido[4,5-c] pyridazines [37]. The foregoing compounds have pesticidal, antitumor, antimicrobial, immunosuppressive, nootropic and antihypertensive and antiallergic activity.

Only a few examples are known of the formation of the pyrano[2,3-d ]6,5-d']dipyridimine system by the interaction of barbituric acids with 3-acylchromones [38, 39]. There is no information as to their biological activity. At the same time, available information on the biological activity of 5-substituted barbituric acids and condensed systems containing the pyrimidine ion fragment, as stated above, indicates that they have varying degrees of biological activity. The effectiveness of many of the substances that have been studied, however, is not satisfactorily high, and many of them are toxic and cause side-effects. Furthermore, bacteria, viruses and tumor cells rapidly develop resistance to the existing drugs, making their employment inefficient [40–46].

The material above suggests the potential usefulness of conducting a scientific search in the area of the synthesis of effective new biological substances by condensing barbituric acids with carbonyl compounds, producing, specifically, derivatives of pyrano[2,3-d:6,5-d']dipyrimidine. The prototype of the invention, i.e., the substance closest in chemical nature to the claimed substance, is 1,3,7,9-tetramethyl-5-(3-chromonyl)-5H-pyrano[2,3-d:6,5-d']dipyrimidino-2,4,6,8 (1H,3H,7H,9H)-tetraon [38]. It is obtained by heating 1,3-dimethylbarbituric acid with 3-chromoncarbaldehyde, first in a mixture with pyridine and triethylamine, and then in acetic acid containing sulfur. As noted above, available sources contain no information on its biological activity.

OBJECT OF THE INVENTION

The object of the invention is to create new substances having antimicrobial, antiviral immunomodulating and antitumor activities.

ESSENCE OF THE INVENTION

The object of the invention is achieved by the synthesis of novel compounds—derivatives of pyrano[2,3-d:6,5-d'] dipyrimidine of general formula:

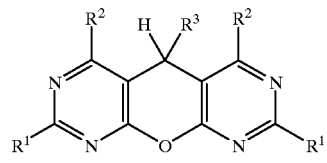

where:
$R^1$ is selected from the group HYDROXY GROUP, MERCAPTO GROUP, HALOGEN,
$R^2$ is selected from the group HYDROXY GROUP, ALKOXY GROUP, HALOGEN,
$R^3$ is selected from the group HYDROGEN, ARYL.

The best variants of the claimed substances are when

| | |
|---|---|
| $R^1 = R^2 = OH, R^3 = 4\text{-}O_2NC_6H_4$ | (I), |
| $R^1 = R^2 = Cl, R^3 = C_6H_5$ | (II), |
| $R^1 = R^2 = OH, R^3 = 4\text{-}IC_5H_4$ | (III), |
| $R^1 = R^2 = OH, R^3 = H$ | (IV), |
| $R^1 = OH, R^2 = OCH_3, R^3 = 4\text{-}O_2NC_6H_4$ | (V), |
| $R^1 = R^2 = OH, R^3 = 4\text{-}ClC_6H_4$ | (VI), |
| $R^1 = R^2 = OH, R^3 = 4\text{-}BrC_6H_4$ | (VII), |
| $R^1 = SH, R^2 = OH, R^3 = 4\text{-}ClC_6H_4$ | (VIII), |
| $R^1 = SH, R^2 = OH, R^3 = 4\text{-}O_2NC_6H_4$ | (IX). |

It should be noted at once that the use of other representatives of the alkoxy group, the mercapto group, halogens and aryls does not differ in principal in the synthesis process or in the biological activities of the substances obtained, i.e., it is not the specific elements in the $R^1$, $R^2$ and $R^3$ radicals that are of importance, but that they belong to the groups cited in the general formula.

The proposed best variants are listed in the table that follows for clarity.

| Variant | $R^1$ | $R^2$ | $R^3$ |
|---|---|---|---|
| I | OH | OH | $4\text{-}O_2NC_6H_4$ |
| II | Cl | Cl | $C_6H_5$ |
| III | OH | OH | $4\text{-}IC_5H_4$ |
| IV | OH | OH | H |
| V | OH | $OCH_3$ | $4\text{-}O_2NC_6H_4$ |
| VI | OH | OH | $4\text{-}ClC_6H_4$ |
| VII | OH | OH | $4\text{-}BrC_6H_4$ |
| VIII | SH | OH | $4\text{-}ClC_6H_4$ |
| IX | SH | OH | $4\text{-}O_2NC_6H_4$ |

The general formula of the claimed substances and all of the variants of specific compounds listed above are new, and are not known to us from available sources of information. Furthermore, their synthesis and the existence of marked biological activity in them does not follow obviously from the current level of technology, i.e., they are not obvious to one skilled in the art.

DISCLOSURE OF THE INVENTION

The essence of the invention is explained below by five general examples of the synthesis of the claimed substances, the three best claims for synthesis variants known to the inventors as of the date of delivery of the application, three summary tables of the chemico-physical characteristics of the claimed substances giving their yields, melting points, as well as the results of four series of experiments to determine the comparative medico-biological properties of the claimed substances (with corresponding Tables of Quantitative Measurements), where:

EXAMPLE 1

Variant of the Synthesis of 5-Aryl-2,4,6,8-tetrahydroxy-5H-pyrano[2,3-d:6,5-d']dipyrimidines (I, III, IV, VI, VII) and 5-aryl-4,6-dihydroxy-2,8-dimercapto-5H-pyrano[2,3-d:6,5-d']dipyrimidines (VIII, IX)

EXAMPLE 2

Variant of the Synthesis of 5-Aryl-2,4,6,8-tetrahydroxy-5H-pyrano[2,3-d:6,5-d']dipyrimidines (I, III, IV, VI, VII) and 5-aryl4,6-dihydroxy-2,8-dimercapto-5H-pyrano[2,3-d:6,5-d']dipyrimidines (VIII, IX)

EXAMPLE 3

Variant of the Synthesis of 2,4,6,8-Tetrahydroxy-5-(p-nitrophenyl)-5H-pyrano[2,3-d:6,5-d']dipyrimidine (I)

EXAMPLE 4

Variant of the Synthesis of 5P-Phenyl-2,4,6,8-tetrachloro-5H-pyrano[2,3-d:6,5-d']dipyrimidine (II)

EXAMPLE 5

Variant of the Synthesis of 2,8-Dihydroxy-4,6-dimethoxy-5-(4-nitrophenyl)-5H-pyrano[2,3-d:6,5-d']dipyrimidine (V)

EXAMPLE 6

Best Variant Known to the Inventors for the Synthesis of 4-6-Dihydroxy-2,8-dimercapto-5-(p-nitrophenyl)-5H-pyrano[2,3-d:6,5-d']dipyrimidine (IX)

EXAMPLE 7

Best Variant Known to the Inventors for the Synthesis of 5-Phenyl-2,4,6,8-tetrachloro-5H-pyrano[2,3-d:6,5-d']dipyrimidine (II)

EXAMPLE 8

Best Variant Known to the Inventors for the Synthesis of 2,8-Dihydroxy-4,6-dimethoxy-5-(4-nitrophenyl)-5H-pyrano[2,3 -d:6,5-d']dipyrimidine (V)

Table 1—PMR spectra of solutions of claimed substances—derivatives of 5H-pyrano[2,3-d:6,5-d']dipyrimidines—in DMSO-$d_6$ ($\delta$, ppm)

Table 2—$^{13}$C NMR spectra of solutions of claimed substances—derivatives of 5H-pyrano[2,3-d:6,5-d'] dipyrimidines—in DMSO-d$_6$ (δ, ppm)

Table 3—yields, temperatures of decomposition and elemental analysis of claimed substances—derivatives of 5H-pyrano[2,3-d:6,5-d']dipyrimidines Experiment 1 (with Table 4)—determination of the activity of claimed compounds on herpes simplex virus Experiment 2 (with Table 5)—determination of the interferon-inducing activity of claimed compounds.

Experiment 3 with (Table 6)—determination of activity of claimed compounds on C. trachomatis.

Experiment 4 (with Table 7)—determination of acute toxicity of claimed compounds.

EXAMPLE 1

Variant of the Synthesis of 5-Aryl-2,4,6,8-tetrahydroxy-5H-pyrano[2,3-d:6,5-d']dipyrimidines (I, III, IV, VI, VII) and 5-aryl4,6-dihydroxy-2,8-dimercapto-5H-pyrano[2,3-d:6,5-d']dipyrimidines (VIII, IX)

A mixture of 3 mmol of the pyridine salt of 5,5'-arylidenebis(2-thio)barbituric acid and 55 mmol of POCl$_3$ is heated with stirring to boiling. After the precipitate is dissolved (after~1 hour), 3.5 mmol of P$_2$O$_5$ is added to the mixture. The boiling mixture is stirred for 5–7 hours, and then poured into 150–200 ml of cold water and left over night. The precipitate that comes out of solution is filtered, washed with ethanol or acetone, recrystallized from water. Yield 20–30%.

EXAMPLE 2

Variant of the Synthesis of 5-Aryl-2,4,6,8-tetrahydroxy-5H-pyrano[2,3-d:6,5-d']dipyrimidines (I, III, IV, VI, VII) and 5-aryl-4,6-dihydroxy-2,8-dimercapto-5H-pyrano[2,3-d:6,5-d']dipyrimidines (VIII, IX)

A mixture of 0.04 mol of the pyridine salt of 5,5'-arylidenebis(2-thio)barbituric acid, 0.035 mol of POCl$_3$, 0.02 mol of P$_2$O$_5$, and 7–10 ml of chloroform are stirred while being boiled for 4 hours. The reaction mixture is poured into 100 ml of cold water and left over night. Separation and purification of the resulting substances is as described above. Yield 23–86%.

EXAMPLE 3

Variant of the Synthesis of 2,4,6,8-Tetrahydroxy-5-(p-nitrophenyl)-5H-pyrano[2,3-d:6,5-d']dipyrimidine (I)

To a mixture of 3.4 mmol of 2,8-dihydroxy4,6-dimethoxy-5-(p-nitrophenyl)-5H-pyrano[2,3-d:6,5-d'] dipyrimidine, 10 ml of acetic acid, and 10 ml of acetic anhydride there are added 8–12 drops of concentrated sulfuric acid. The mixture is stirred while being boiled for 8–10 hours, and then poured into 150 ml of cold water and left over night. Separation and purification of the resulting substances is as described above. Yield 25–30%

EXAMPLE 4

Variant of the Synthesis of 5P-Phenyl-2,4,6,8-tetrachloro-5H-pyrano[2,3-d:6,5-d']dipyrimidine (II)

A mixture of 3 mmol of the pyridine salt of 5,5'-benzylidenebisbarbituric acid and 55 mmol of POCl$_3$ is heated with stirring to boiling. After the precipitate dissolves (about 1 hour), 3.5 mmol of P$_2$O$_5$ are added to the solution. The boiling mixture is stirred for 4 hours and then poured into 150–200 ml of cold water and left over night. The precipitate that comes out of solution is filtered and washed with ethanol or acetone. Yield 10%.

EXAMPLE 5

Variant of the Synthesis of 2,8-Dihydroxy-4,6-dimethoxy-5-(4-nitrophenyl)-5H-pyrano [2,3-d:6,5-d']dipyrimidine (V)

A mixture of 14 mmol of 6-methoxyuracil, 7 mmol of p-nitrobenzaldehyde, 10 ml of acetic acid and 10 ml of acetic anhydride are stirred at 110–115° C. for 3–5 h. The precipitate that comes out of solution is filtered, washed with ethanol and dried.

Examples of the Best Variants of the Synthesis of the Claimed Substances of Formula (I) Known to the Inventors.

EXAMPLE 6

Best Variant for the Synthesis of 4-6-Dihydroxy-2,8-dimercapto-5-(p-nitrophenyl)-5[-pyrano[2,3-d:6,5-d:']dipyrimidine (IX)

A mixture of 0.04 mmol of the pyridine salt of 5,5'-(p-nitrobenzylidene)bis(2-thiobarbituric) acid, 0.035 mol of POCl$_3$, 0.02 mol of P$_2$O$_5$ and 7–10 ml of chloroform are stirred while boiling for 4 hours. Then the reaction mixture is poured into 100 ml of cold water and left over night. Separation and purification of the resulting substances are as described above. Yield 85%.

EXAMPLE 7

Best Variant Known to the Inventors for the Synthesis of 5-Phenyl-2,4,6,8-tetrachloro-5H-pyrano[2,3-d:6,5-d']dipyrimidine (II)

A mixture of 3 mmol of the pyridine acid of 5,5'-benzylidenebisbarbituric acid and 55 mmol of POCl$_3$ is heated with stirring to boiling. After the precipitate dissolves (about 1 hour), 3.5 mmol of P$_2$O$_5$ are added to the solution. The boiling mixture is stirred for 4 hours and then poured into 150–200 ml of cold water and left over night. The precipitate that comes out of solution is filtered and washed with ethanol or acetone. Yield 10%.

EXAMPLE 8

Best Variant of the Synthesis of 2,8-Dihydroxy-4,6-dimethoxy-5-(4-nitrophenyl)-5H-pyrano[2,3-d:6.5-d']dipyrimidine (V)

A mixture of 14 mmol of 6-methoxyuracil, 7 mmol of p-nitrobenzaldehyde, 10 ml of acetic acid and 10 ml of acetic anhydride are stirred at 110–115° C. for 3–5 h. The precipitate that comes out of solution is filtered, washed with ethanol and dried. Yield 46%.

TABLE 1

PMR spectra of solutions of claimed substances — derivatives of 5H-pyrano[2,3-d:6,5-d'] dipyrimidines — in DMSO-$d_6$ ($\delta$, ppm)

| No | $C^5$ | Ar | NH |
|---|---|---|---|
| I | 4.62 s | 7.60 d (2H, $H^{2\text{-}6}$), 8.08 d (2H, $H^{3\text{-}5}$), J 8.4 Hz | 11.18 s, 12.35 narr. s. |
| II | 5.43 s | 7.32 M (3H), 7.40 d (2H, J 7.4 Hz) | — |
| III | 4.45 s | 7.10 d (2H, $H^{2\text{-}6}$), 7.57 d (2H, $H^{3\text{-}5}$), J 8.1 Hz | 11.14 s, 12.20 narr. s. |
| IV | 2.86 s | — | 11.19 s, 12.06 |
| V | | | |
| VI | 4.48 s | 7.26 d (2H, $H^{2\text{-}6}$), 7.31 d (2H, $H^{3\text{-}5}$), J 8.3 Hz | 11.16 s, 12.30 narr. s. |
| VII | 4.48 s | 7.25 d (2H, $H^{2\text{-}6}$), 7.40 d (2H, $H^{3\text{-}5}$), J 8.2 Hz | 11.14 s, 12.30 narr. s. |
| VIII | 4.51 s | 7.27 d (2H, $H^{2\text{-}6}$), 7.34 d (2H, $H^{3\text{-}5}$), J 8.4 Hz | 12.52 s |
| IX | 4.84 s | 7.62 d (2H, $H^{2\text{-}6}$), 8.09 d (2H, $H^{3\text{-}5}$), J 8.4 Hz | 12.53 s |

TABLE 2

$^{13}$C NMR spectra of solutions of claimed substances — derivatives of 5H-pyrano[2,3-d:6,5-d'] dipyrimidines — in DMSO-$d_6$ ($\delta$, ppm)

| No | $C^5$ | $C^{4a,5a}$ | $C^{2,8}$ | $C^{4,6,9a,10a}$ | Ar |
|---|---|---|---|---|---|
| I | 32.57 | 89.45 | 152.35 | 149.30, 162.57 | 122.92 ($C^{3\text{-}5}$), 129.83 ($C^{2\text{-}6}$), 146.21 ($C^1$), 151.09 ($C^4$) |
| II | 39.12 | 115.40 | 156.99 | 161.34, 163.21 | 128.14 ($C^4$), 128.65 ($C^{3\text{-}5}$), 129.80 ($C^{2\text{-}6}$), 137.98 ($C^1$) |
| III | 31.99 | 90.03 | 152.19 | 149.38, 162.57 | 92.32 ($C^4$), 130.79 ($C^{2\text{-}6}$), 136.54 ($C^{3\text{-}5}$), 143.41 ($C^1$) |
| IV | 15.24 | 85.62 | 152.08 | 149.36, 163.56 | — |
| VI | 31.75 | 90.01 | 152.14 | 149.35, 162.52 | 127.66 ($C^{2\text{-}6}$), 130.17 ($C^{3\text{-}5}$), 130.95 ($C^4$), 142.48 ($C^1$) |
| VII | 31.82 | 89.96 | 152.14 | 149.33, 162.51 | 119.47 ($C^4$), 130.57 ($C^{2,3,5,6}$), 142.90 ($C^1$) |
| VIII | 32.53 | 94.69 | 173.94 | 160.33 | 127.81 ($C^{2\text{-}6}$), 130.45 ($C^{3\text{-}5}$), 131.55 ($C^4$), 141.27 ($C^1$) |
| IX | 33.61 | 93.63 | 173.99 | 149.78, 160.36 | 123.10 ($C^{3\text{-}5}$), 130.13 ($C^{2\text{-}6}$), 146.39 ($C^1$), 152.73 ($C^4$) |

TABLE 3

Yields, temperatures of decomposition and elemental analysis of claimed substances — derivatives of 5H-pyrano[2,3-d:6,5-d'] dipyrimidines

| No | Yield % | Temp. decomp °C. | Found, % C | H | N | Formula | Calculated, % C | H | N |
|---|---|---|---|---|---|---|---|---|---|
| I | 23 | >300 | 48.26 | 2.76 | 18.64 | $C_{15}H_9N_6O_7$ | 48.53 | 2.44 | 18.86 |
| II | 10 | 190 | 44.78 | 1.34 | 14.25 | $C_{15}H_6Cl_4N_4O$ | 45.04 | 1.50 | 14.00 |
| III | 33 | >300 | 40.03 | 2.31 | 12.04 | $C_{15}H_9IN_4O_5$ | 39.84 | 2.01 | 12.36 |
| IV | 48 | >300 | 55.13 | 2.89 | 17.02 | $C_{16}H_{10}N_4O_5$ | 55.22 | 3.09 | 17.17 |
| V | 46 | 294 | 51.23 | 3.37 | 17.44 | $C_{17}H_{13}N_5O_7$ | 51.13 | 3.28 | 17.54 |
| VI | 47 | >300 | 48.30 | 3.24 | 14.36 | $C_{16}H_9ClN_4O_5$ | 49.95 | 2.51 | 15.53 |
| VII | 29 | 310 | 44.75 | 2.15 | 13.97 | $C_{16}H_9BrN_4O_5$ | 44.47 | 2.24 | 13.83 |
| VIII | 58 | 265 | 45.94 | 2.23 | 14.40 | $C_{16}H_9ClN_4O_3S_2$ | 45.86 | 2.31 | 14.26 |
| IX | 86 | 268 | 44.32 | 2.18 | 17.41 | $C_{15}H_9N_5O_5S_2$ | 44.66 | 2.25 | 17.36 | dard method [41, 42]. The virus was grown on a reinoculated Vero cell culture obtained from the cell culture bank of the Institute of Cytology of the Russian Academy of Sciences.

Procedure

To cells grown on medium RPMI-1640 with 10% calf serum and placed in the wells of a 96-well plate, the virus was added to give a final concentration of 10 particles/ml and the claimed compounds dissolved in DMSO were added to give a final concentrations of 100, 10, and 1 mg/l. We used 5 individual wells for every concentration tested. The plate was incubated for 60 min at 38° C. in a CO2 incubator. After incubation the virus was removed and new medium was added that contained the claimed compounds in the test concentrations.

The results were evaluated according to the existence of a cytopathic action of the virus on the cells after 36 hours of incubation at 38° C. in the CO2 incubator.

The following controls were used in the experiment:
1. Control of culture cells (capability for normal growth).
2. Control of virus (assessment of reproductive capability).
3. Control of antiviral activity of an antiviral preparation—acylcovir.
4. Control of compounds (toxicity of compounds).
5. Control of solvent (DMSO) on toxicity.

To access the cytopathic effect of the virus, we counted the number of unchanged cells in 100 fields formed by a specialized grid on the eyepiece of the inversion microscope. The results are presented in Table 4.

EXPERIMENT SECTION

Experiment 1
Determination of the Activity of Claimed Compounds on Herpes Simplex Virus The antiviral activity was studied relative to the virus herpes simplex type I (VPG-I/Leningrad/248/88) by a stan-

TABLE 4

Activity of claimed compounds on herpes simplex virus

| | | Concentration of test compounds (mg/l) | | |
|---|---|---|---|---|
| No. | Compound | 100 | 50 | 10 |
| 1 | Acyclovir | —* | — | 9600** (80%)** |
| 2 | DMSO | 12000 | 12000 | 12000 |
| 3 | Cell control | 12000 | 12000 | 12000 |
| 4 | I | 9600 (80%) | 8400 (70%) | 7200 (60%) |
| 5 | II | Cytotoxic | Cytotoxic | — |
| 6 | III | 4800 (40%) | — | — |
| 7 | IV | Cytotoxic | — | — |
| 8 | V | 6000 (50%) | — | — |
| 9 | VI | 6000 (50%) | — | — |
| 10 | VII | 3600 (30%) | — | — |
| 11 | VIII | 10800 (90%) | 6000 (50%) | 2400 (20%) |
| 12 | IX | 4800 (40%) | — | — |

*the indicated concentration of the drug was not tested,
**number of cells in 100 fields,
***the number in parentheses is the percent protection of the cells against the virus compared to the cell culture control.

The results presented in Table 4 indicate that all of the claimed compounds exhibit antiherpes activity comparable to that of the standard drug acyclovir. The other claimed compounds exhibited less marked activity in suppressing the reproduction of the virus under the experimental conditions selected.

Experiment 2
Determination of the Interferon-inducing Activity of Claimed Compounds Interferon synthesis induction by the claimed preparations was conducted on a primary culture of human lymphocytes (the cells in the human body are the main producers of interferon). To obtain a culture of the lymphocytes we used fresh blood (12 hours after collection) from healthy animals (not from the second group). To isolate the lymphocytes, heparinized blood obtained from a healthy donor was centrifuged in a density gradient (phycoll-verographin) of 1.71 g/cm$^3$ to isolate the fraction of the immunocompetent cells. This fraction was taken and diluted with RPMI-1640 nutrient medium containing 5% bovine fetal serum, 0.3 mg/ml of L-glutamine, 100 units/ml of penicillin, and 50 mg/ml of streptomycin. The lymphocyte concentration was determined after staining with methyl blue and the number of cells in the Goryaev chamber was calculated. The starting solutions of the claimed substances were diluted with RPMI-1640 nutrient medium to give final concentrations of the substances of 100 mg/l, 10 mg/l, and 1 mg/l after the lymphocyte suspension was added. The final concentration of the lymphocytes in the induction mixture was 3·10$^6$ cells/ml. The following controls were processed in parallel with the test samples:

1) control for the spontaneous production of interferon (IFN) by lymphocytes;
2) control for the process occurring under the action of standardized INF inducer N-methyl-N-(a,D-glucopyranosyl)ammonium 10-methylene carboxylate of acridone (cycloferon).
3) control for the process occurring under the action of standardized INF inducer Neovir with the corresponding content of DMSO in the experimental samples.
4) control for the spontaneous production of interferon in the presence of DMSO in a quantity corresponding to the test samples.

The control and the experimental samples were incubated for 24 hours at 37° C. Following incubation the samples were centrifuged at 2000 g to settle out the cellular elements and the INF-containing supernatant was taken from the samples and analyzed for INF content. The cell residue was resuspended in the same volume of nutrient medium, stained with a vital dye—trypan blue—and the number of cells in the Goryaev chamber was calculated (as described above) to determine the cytotoxic activity of the preparations.

For the quantitative determination of INF in the control and experimental samples we used the ProCon IF2 Plus immunoenzyme test system sold by TOO Proteinovyi Kontur. To determine the quantity of interferon s in the sample we used a solid-phase immunoenzyme method utilizing horseradish peroxidase as the enzyme indicator. The activity of the bound peroxidase was measured using an automated photometer at a wavelength of 450 nm for the microplanchets with a microprocessor. To calculate the results we determined in parallel the activity of INF in standard solutions of INF containing known amounts of the preparation. On the basis of the results obtained we plotted a calibration curve that allowed us to obtain data expressed in International Units (IU) from the microprocessor of the automated photometer. The results of the analysis are expressed in IU of activity of INF per ml in the given induction system containing 3·10$^6$ lymphocytes/ml. Every experimental and control point was studied in 4 parallel runs.

Controls of the Immunoenzyme Reaction
1. Control of DMSO with the nutrient medium.
2. Control of the system components (according to Instructions). All results were taken into account only if the controls corresponded to the passport data of the system.

The results obtained were analyzed statistically using the t-test and the confidence interval at p=0.05 was calculated. Analysis of the convergence of the results of the parallel tests were performed. As a result of the experiment it was established that all of the claimed compounds have an ability to induce INF synthesis entirely comparable to that of known interferon-inducing substances, which demonstrates their antiviral and antitumor effectiveness (Table 5).

TABLE 5

Quantitative assessment of IFN-inducing activity of claimed compounds. Content of INF in induction mixture after 24 hours of incubation with various concentrations of the drugs.

| | | Interferon-inducing activity of the drug at different concentrations (mg/ml), IU/3 · 10$^4$ lymp/ml | | |
|---|---|---|---|---|
| No. | Compound | 100 mg/ml | 10 mg/ml | 1 mg/ml |
| 1. | Lymphocyte control | 0 | 0 | 0 |
| 2. | Cycloferon | 58.0 ± 1.4 | 22.0 ± 2.5 | 3.8 ± 0.8 |
| 3. | Neovir | 66.0 ± 1.4 | 24.5 ± 1.2 | 4.1 ± 0.5 |
| 4. | Poly I/poly C | —* | 43.6 ± 2.0 | 10.5 ± 0.8 |
| 5. | DMSO | 0 | 0 | 0 |
| 6. | I | 80.0 ± 1.2 | 28.0 ± 1.5 | 8.0 ± 0.8 |
| 7. | II | 40.0 ± 1.4 | 16.0 ± 0.8 | 2.0 ± 0.4 |
| 8. | III | 243.2 ± 1.0 | 112.6 ± 2.0 | 56.5 ± 1.0 |
| 9. | IV | 74.0 ± 1.8 | 29.9 ± 2.0 | 3.8 ± 1.5 |
| 10. | V | 108.9 ± 2.0 | 50.6 ± 1.8 | 10.5 ± 2.5 |
| 11. | VI | 92.2 ± 2.1 | 36.9 ± 1.2 | 6.5 ± 1.4 |
| 12. | VII | 22.2 ± 1.4 | 10.6 ± 1.8 | 5.6 ± 1.6 |
| 13. | VIII | 70.5 ± 2.5 | 23.2 ± 1.5 | 1.5 ± 1.0 |
| 14. | IX | 64.0 ± 1.8 | 28.0 ± 2.5 | 6.8 ± 2.0 |

*the preparation was not tested in this concentration

Experiment 3

Determination of Activity of Claimed Compounds on *Chlamydia trachomatis*

The antimicrobial activity of the claimed compounds was studied on *C. trachomatis* D323—a standard strain from the collection of the Department of Microbiology of the Pavlov St.-Petersburg State University. This strain was isolated from a patient with chlamydic urethritis. It has the morphology and physiological activity characteristic of the species, and is sensitive to the action of drugs used in treating chlamydic infections.

In the work reported here we used McCoy and L929 cell cultures obtained from the Institute of Cytology of the Russian Academy of Sciences.

Procedure

The cells were grown in flasks of neutral glass in RPMI-1640 medium with an addition of 10% fetal calf serum. The experiment was placed in glass (toxicity-free) flat-bottomed flasks and covered with glass. The cells were introduced into the medium in a final concentration of $1 \cdot 10$ cells/ml. After a monolayer was obtained, standard infectious doses of chlamydia that had been maintained in a frozen state at $-70°$ C. were added to test tubes. At the same time, the test compounds were added to the cells to give a final concentration of 100 mg/ml. The sample was centrifuged at 2400 g for 60 min at room temperature and incubated at 37° C. for 2 hours. After this, the nutrient medium was replaced by a new medium that contained 5% fetal calf serum and cycloheximide (2 $\mu$g/ml) and the claimed compounds were readded in the same concentration. A parallel series of samples was run using medium without the cycloheximide in order to avoid its influence on the test substances. The samples were incubated for 48 hours in a CO2 incubator.

The controls included: controls of the cell cultures, control for the action of solvents, control for the action of chlamydia in the absence of any preparations at all, control for the sensitivity of chlamydia to standard antimicrobial preparations—cyprofloxacin and abactal [46], control of the test compounds on toxicity relative to cell cultures.

The results were evaluated from the detection of chlamydia cytoplasmatic inclusion by an immunoenzyme method (MicroTrac *Chlamydia trachomatis* Direct Specimen Test) and from chlamydia antigens using CylaMonoScreen (Russian-British Joint Venture, 66 Regent's Park Road, London NW 1 7SX) [46]. The effect of the preparations was determined by analyzing the state of the monolayer and the number of cells with CPE based on a comparison to the control (cell culture infected with *C. trachomatis* D323) by counting the number of unchanged cells in 100 viewing fields produced by a specialized grid for the microscope eyepiece.

The results of the control samples satisfying the requirements of the experiment:

control of cell culture—the morphology of the cells and the state of the monolayer are appropriate to the given type of cells, control of growth of chlamydia in the cell culture—the existence of CPE in the monolayer, control of the action of a standard antimicrobial preparation—a reduction in the number of cells with CPE in the monolayer compared to the previous control, control of toxicity of claimed compounds—no toxicity, control for the activity of solvents—no toxic effect on the cells. The results of the tests are presented in Table 5.

TABLE 6

Activity of claimed compounds on *C. trachomatis*

| No. | Compound | Concentration of test compounds (mg/l) | |
|---|---|---|---|
| | | 100 | 30 |
| 1. | Cell control | 8000* | 8000 |
| 2. | DMSO | 8000 | 8000 |
| 3. | Control of inf. cells | 6400 | 6400 |
| 4. | I | 7640 (80%)** | 7520 (70%) |
| 5. | II | cytotoxic | cytotoxic |
| 6. | III | cytotoxic | — |
| 7. | IV | cytotoxic | 7040 (40%) |
| 8. | V | cytotoxic | — |
| 9. | VI | 6560 (15%) | — |
| 10. | VII | cytotoxic | — |
| 11. | VIII | 7360 (60%) | — |
| 12. | IX | 7360 (60%) | — |
| 13. | Cyprofloxacin | 7200 (50%) | 6880 (30%) |
| 14. | Abactam | 7200 (50%) | 7040 (40%) |

*number of cells in 100 fields,
**the number in parentheses is the percent protection of the cells against infection,
***the indicated concentration of the drug was not tested.

The data obtained demonstrate that the claimed compounds can be used to treat illnesses caused by chlamydia.

Experiment 4

Determination of Acute Toxicity

Acute toxicity was determined on non-linebred white mice weighing 18–20 g. Emulsions of certain of the claimed compounds were prepared in a range of concentrations: 1500, 700, 500, 100, 20 and 5 $\mu$g/kg. Five animals were used to study each specific concentration of a compound. The preparation was administered once a day by mouth or intravenously. The observation period was 14 days On days 1, 8 and 15 the animals in every group were weighed. For a control we used animals who received the emulsion without the test compounds.

All animals, both that died in the course of the experiment and those that survived to the end of the experiment, were opened to allow macroscopic examination of internal organs.

In the course of the experiment no loss of weight was observed or any change in behavior or external appearance, nor was there any loss of life. Based on the results of the macroscopic examination of internal organs of the animals in the test and the control groups, no pathological findings were made (Table 7).

TABLE 7

Acute toxicity (LD 50) of some of the claimed compounds

| No. | Compound | LD50, mg/kg |
|---|---|---|
| 1. | I | 1600 |
| 2. | VIII | 1800 |

The data show that when the claimed compounds were taken by mouth or intravenously at a dosage level of 1500 mg/kg, no acute toxicity was found for mice.

Industrial Application

Examples 1–8 of the practical synthesis and the chemico-physical analysis of the claimed compounds listed in Tables 1–3 confirm the possibility of the laboratory and industrial synthesis of all nine claimed compounds, which are capable of being manufactured by the modern pharmaceutical industry, as well as their precise identification using standard control methods.

The series of experiments on identifying the biological properties presented in the four reports presented showed that the claimed compounds exhibit biological activity relative to a variety of microorganisms, including chlamydia, herpes simplex virus, and also have interferon-inducing activity. This last suggests the possibility of using them to treat herpes, other viral and certain tumor illnesses. The information presented above prove that the goal of the invention was achieved, namely, the synthesis of a novel class of heterocyclic compounds having a high and broad biological activity, in particular, immunostimulating, antichlamydic and antiviral activities.

Thus, we believe that the claimed compounds (novel substances) satisfy all requirements for a patent: they are novel, non-obvious, and can be produced on an industrial basis.

References

1. Pharmaceutical microbiology, Ed. by W. B. Hugo and A. D. Russel Blackwell Scientific Publications, Oxford, 1987, 511 p.
*2. Машковский М.Д Лекарственные средства Пособие по фармакотерапии для врачей Вильнюс Гамта 1993 Ч 1,544 с.
3. Sans R. G., Chosas M. G. // Pharmazie, 1998, Bd 43, N 12, S. 827–829.
4. Singh A., Mohan R. R., Misra V. S. // Indian Drugs., 1985, Vol.22. N 8, P. 418–422 (Chemical Abstracts, Vol 104, 129855c).
5. Singh S., Gupta G. P., Shanker K. // Indian J. Chem., 1985 Vol. 24, B N 10, P. 1094–1097.
6. Singh A., Misra V. S. // Pharmacol. Res., 1989 Vol. 21, N 1, P. 59–64 (Chemical Abstracts, Vol. 111, 4990z).
7. Kumar P., Nath C., Agarwal J. C., Bhargava K. P., Shanker K. // India J. Chem., 1983, Vol. 22B, N 9, P. 955–958.
* 8. Патент Японии М КЛ A 61K 31/505, No 05213755, аявлен Jul. 2, 1992 (92/56671), опубликован Aug. 8, 1993 (Chemical Abstracts, 1993 Vol. 119,262520r).
9. Kumar A., Singh S., Saxena A. K., Shanker K. // Indian J. Chem., Sect. B., 1988, Vol. 27N5, P. 443–447.
* 10. Hirota K., Fukazawa T., Isobe Y., Morita H., заявка ЕПВ No.546661, М КЛ С 07D 239/62, заявлен Sep. 10, 1991 (91/290538), опубликован Jun. 6, 1993 (Chemical Abstracts, Vol. 119. 180814a).
*11. Барам Н.И Х. Зияев, Л, z, 24 Г.А. Биктимиров Л. Исмаилов А. И, Ура3МеТОВ К.Г. // Химия природных соединений 1988, No 5, С. 647–650.
12. Kreutzberger A., Kreutzberger E. // Arch. Pharm., 1983 Bd 316H. 1S. 6–9.
* 13. Minatelli J. A., Brewer A. D., заявка Германии М КЛ С 07D 471/04, No 3446371, заявлен Dec. 19, 1983. опубликована Jun. 27, 1985 (Chemical Abstracts, Vol. 104, 19602k).
* 14. Brewer A. D., Патент США No 4920126, М КЛ A 61K 31/50, НКНКИ 514–274, аявлен Oct. 5, 1988, опубликован Apr. 4, 1990 (Chemical Abstracts, Vol. 113, 165414c).
15. Kratt G., Salbeck G., Bonin W., Duewel D., За аявка Германии М КЛ С 07D 239/62. No. 3903404, аявлен Jun. 2, 1989, опубликован Sep. 8, 1990 (Chemical Abstracts, Vol. 114, 23984k).
* 16. De Sousa B., Muntwyler R., Schmidt W., Ciba-Geigy A.-G., П653840 (1986). Швейцария (Chemical Abstract, Vol. 106,98105t).
* 17. Naka T., Nagaoka A., Furukawa Y., Заявка ЕПВ No. 237289 (1987).
* 18. Yoneda F., Sasaki T., Патент М КЛ С 07D 471/104, No. 03 81276, Заявлена Aug. 8, 1989 (89/218146), опубликована May 4, 1991 (Chemical Abstracts, Vol. 115, 255902f).
19. Kimachi T., Yoneda F., Sasaki T. // Heterocycl. Chem., 1992, Vol. 29, N 4P. 763–765.
* 20. Jiang J. B., Isaacson D, Патент США М КЛ С 07D 471/04, НКИ 544–250, No. 4656274, Заявлен Dec. 2, 1985, опубликован Jul. 4, 1987 (Chemical Abstracts, Vol. 107, 39643g).
21. Cowden W. B., Clark I. A., Hunt N. H. // J. Med. Chem., 1988, Vol. 31, N 4, P. 799–801.
* 22. Cowden W. B., Clark I.A., Заявка PCT WO 88 04658, М КЛ C07D 474/14, Заявлена Dec. 17, 1986 (86/9548), опубликована Jun. 6, 1988 (Chemical Abstracts, Vol. 109, 210800f).
23. Quijano M. L., Nogueras M., Melguizo M., Alvarez de Cienguegos G., Melgarejo M., Sanches A. // Nucleosides & Nucleotides, 1989, VOl. 8, N 8, P. 1519–1528.
* 24. Gauri K. K., Erbler H., Eltze M., Заявка ЕПВ, М КЛС 07D 487/104, No. 61381, Заявлена Jun. 13, 1984 (81/2621), опубликована Oct. 27, 1982 (Chemical Abstracts, Vol. 98, 126148w).
25. Ahluwalia V.K., Batla R., Khurana A., Kumar R. // Indian J. Chem., 1990, Vol. 29B, N 12, P. 1141–1142.
26. Joshi K. C., Jain R., Sharma K., Bhattacharya S. K., Goel R. K. // J. Indian Chem. Soc., 1988, Vol. 65, N 3,P. 202–204.
*27. Барам Н.И Камаев Ф Г Пайзиева Р.З., Исмаилов А.И // Узбекский химический журнал 1989, N 3, C. 41–43.
28. Das A., Sahu K., Mishra B. K., Behera G. B. // Indian J. Chem., 1985, Vol. 24B, N 3, P. 310–311.
* 29. Cooper K., Заявка PCT, WO 9012015, М КЛ С 07D 519/00, Зопубликована Jan. 4, 1989, приоритет Oct. 18, 1990, Великобритании Патент (Chemical Abstracts, Vol. 114,122404c).
* 30. Jiang J.B., Патент США No. 4596805 (1986). (Chemical Abstracts, Vol. 106, 5070q).
31. Kajino M., Meguro K. Heterocycles (Japan), 1990, Vol. 31, N 12, P. 2153–2161 (Chemical Abstracts, Vol. 114, 207192g).
32. Donkor I., Gangjee A., Kisluik R. L., Gaumont Y. // J. Heterocycl.Chem., 1991, Vol. 28N 7, P. 1651–1655.
33. Wood H. C. S., Wrigglesworth R., Yeowell D. A., Gurney F. W., Hurlbert B. S. // J. Chem. Soc. Perkin Trans. I. 1974, N 11, P. 1225–1230.
34. Nagamatsu T., Yamasaki H., Hirota T., Yamato M., Kido Y., Shibata M., Yoneda F. // Chem. Pharm. Bull., 1993, Vol. 41, N 2, P. 363–368.
35. Motawia M. S., Joergensen P. T., Larnkjaer A., Pedersen E. B., Nielsen C. // Monatsh. Chem., 1993, Bd 124, H. 1, S. 55–64.
36. Ahluwalia V. K., Batla R., Khurana A., Kumar R. // Indian J. Chem., 1990 Vol. 29B, N 12, P. 1141–1142.

37. Billings B. K., Wagner J. A., Cook F. D., Castle R. N. // J. Heterocycl. Chem., 1975Vol. 12N 6, P. 1221–1224.
* 38. Eiden F., Fenner H. // Chemische Berichte, 1968, Bd 101, N 8, S. 2894–2898. -прототип..
39. Eiden F., Schikorr W. // Arch. Pharm., 1972, Bd 305N 3, S. 187–193.
* 40. Stone K. M., Wittington W. L., Treatment of genital gerpes, Rev. of infect.
Dis., 1990, 12, Supl. 6, P. 610–619.
* 41. Saltzman R., Jurewicz R., Boon B, Safety of famciclovir in patients with herpes zoster and genital gerpes, Antimic.Agents and Chemother., 1994, 38, 10, P. 2454–2457.
42. Gentry G. A., Lawrency N., Lushbaugh N. Isolation and differentiation of Herpes simplex virus and Trichomonas vaginalis in cell culture. J. of. Clinical Microbiology, 1985, 22, 2, P. 199–204.
43. Judson B. A., Lambert P. P. Improved Syva MicroTrac Clamydia trachomatis direct test method. Journal of Clinical Microbiology, 1988Vol. 26, N12, p.2657–2658.
44. Fenelon L. E., Mumtaz G., Ridgway G. L. The in-vitro susceptibility of Chlamydia pneumoniae, journal of Antimicrobial Chemotherapy, 1990, 26, p. 763–767.
45. Boyd M. R. The Future of new drug development. Current therapy in oncology 1992, 11–22.
46. Grever M. R, Schepartz S. A., Chabner B. A., The National Cancer Institute: cancer drug discovery and development program, Seminars in oncology, 1992, 19, 6, p. 622–638.
* KEY TO TRANSLATION OF REFERENCES
2. Mashkovskii M. D., Medicinal Substances. Pharmacotherapy Guide for Physicians. Vilnius, Gamta, 1993. Part I, 544 pp.
8. Japanese Patent, Int Cl A 61 K 31/505, No. 05213755, filed Jul. 2, 1992 (92/5667 1), published 24.08.1993 (Chemical Abstracts, 1993, Vol. 11o9, 262620g).
10. Hirota K., Fukazawa T., Isoba Y., Morita H., Claim EPU No. 546661, Int Cl C 07D 239/62, filed Sep. 10,1991 (91/290538), published Jun. 16, 1993 (Chemical Abstracts, 1993, Vol. 119, 180814a).
11. Baram N. I., Ziyaev Kh. L., Ismailova G. A., Biktimirov L., Ismailov A. I.,1., Urazmetov K. G.//The Chemistry of Natural Compounds. 1988, No. 5, pp. 647–650.
13. Minatelli J. A., Brewer A. D., German application, Int Cl. C 07D 471/04, No. 3446371, filed Dec. 12, 1983, published Jun. 27, 1985 (Chemical Abstracts, Vol. 104, 19602k).
14. Brewer A. D., U.S. Pat. No. 4,920,126, Int cl A 61 K 31/505, NKI 514–274, filed Oct. 5, 1998, published Apr. 4, 1990 (Chemical Abstracts, Vol. 113, 23984k).
16. De Sousa B., Muntwyler R., Schmidt W., Ciba-Geigy A.-G. Swiss Patent No. 653840 (1986). (Chemical Abstracts, Vol. 106, 98105t).
17. Naka T., Nagaoka A., Furukawa Y. EPU application no. 237289 (1987).
18. Yoneda F., Sasaki T., Japanese Patent Int Cl C 07D 471/04, No. 0381276, filed Aug. 24, 1989 (89/218146), published May 4, 1991 (Chemical Abstracts, Vol. 115, 255902f).
20. Jiang J. B., Isaacson D. U.S. Pat. No. 4,656,274, Int cl C07D 471/04, NKI 544–250, filed Dec. 2, 1985, published Jul. 4, 1987 (Chemical Abstracts, Vol. 107, 39643g).
22. Cowden W. B., Clark 1. A. PCT claim WO 86 04658, Int Cl C07D 474/14, filed Dec. 17, 1986 (86/9548), published Jun. 6, 1988 (Chemical Abstracts, Vol. 109, 210800f).
24. Gauri K. K., Erbler H., Eltze M., EPU application, Int Cl C07D 487/04, No. 61381, filed Jun. 13, 1984 (81/2621), published Oct. 27, 1982. (Chemical Abstracts, Vol. 98, 126148w).
27. Baram N. I., Kamaev F. G., Paizieva R. Z., Ismailov A. //Uzbekskii Khimicheskii Zhurnal. 1989, No. 3, pp. 41–43.
29. Cooper K., PCT application, WO 9012015, Int. Cl. C 07D 519/00, filed Jan. 4, 1989, published Oct. 18, 1990, priority. Great Britain. (Chemical Abstracts, Vol. 114, 122404c).
30. Jiang J. B., U.S. Pat. No. 4,596,805 (1986). (Chemical Abstracts, Vol. 106, 5070q).
38. Eiden F., Fenner H.//Chemische Berichte, 1968, Vol. 101, No. 8, pp. 2894–2898— prototype
39. . . . gential herpes [spelling correction]
41. . . . gential herpes [spelling correction]

What is claimed is:

1. A compound having the formula:

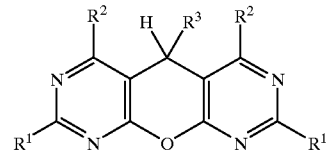

where
R$^1$ is selected from the group consisting of hydroxy group, mercapto group, and halogen;
R$^2$ is selected from the group consisting of hydroxy group, alkoxy group, and halogen; and
R$^3$ selected from the group consisting of hydrogen and aryl, optionally substituted by halogen or nitro.

2. A compound according to claim 1, wherein R$^1$ is OH, R$^2$ is OH, and R$^3$ is 4-O$_2$NC$_6$H$_4$.

3. A compound according to claim 1, wherein R$^1$ is Cl, R$^2$ is Cl, and R$^3$ is C$_6$H$_5$.

4. A compound according to claim 1, wherein R$^1$ is OH, R$^2$ is OH, and R$^3$ is 4-IC$_5$H$_4$.

5. A compound according to claim 1, wherein R$^1$ is OH, R$^2$ is OH, and R$^3$ is H.

6. A compound according to claim 1, wherein R$^1$ is OH, R$^2$ is OCH$_3$, and R$^3$ is 4 -O$_2$NC$_6$H$_4$.

7. A compound according to claim 1, wherein R$^1$ is OH, R$^2$ is OH, and R$^3$ is 4-ClC$_6$H$_4$.

8. A compound according to claim 1, wherein R$^1$ is OH, R$^2$ is OH, and R$^3$ is 4-BrC$_6$H$_4$.

9. A compound according to claim 1, wherein R$^1$ is SH, R$^2$ is OH, and R$^3$ is 4-ClC$_6$H$_4$.

10. A compound according to claim 1, wherein R$^1$ is SH, R$^2$ is OH, and R$^3$ is 4-O$_2$NC$_6$H$_4$.

* * * * *